United States Patent [19]

Yoshikawa et al.

[11] Patent Number: 5,314,807

[45] Date of Patent: May 24, 1994

[54] METHOD FOR PRODUCING AN ANGIOTENSIN CONVERTING ENZYME INHIBITOR-CONTAINING COMPOSITION

[75] Inventors: Masaaki Yoshikawa, Joyo; Keiichi Yokoyama; Masayasu Hasegawa, both of Kyoto; Ryouichi Yasumoto, Kawachinagano; Hiroyuki Fujita, Suita, all of Japan

[73] Assignee: Nippon Gohsei Kagaku Kogyo Kabushiki Kaisha, Osaka, Japan

[21] Appl. No.: 858,842

[22] Filed: Mar. 27, 1992

[30] Foreign Application Priority Data

Mar. 29, 1991 [JP] Japan ................................. 3-142283
Oct. 17, 1991 [JP] Japan ................................. 3-298060

[51] Int. Cl.$^5$ ........................ C10P 21/00; C12N 9/56; C12N 9/58
[52] U.S. Cl. .................................. 435/68.1; 435/219; 435/222; 435/223; 435/225; 435/839; 435/913; 435/918; 435/939
[58] Field of Search ............... 435/68.1, 219, 222, 435/223, 225, 839, 913, 918, 939

[56] References Cited

U.S. PATENT DOCUMENTS

| | | | |
|---|---|---|---|
| 3,655,513 | 4/1972 | Sternberg | 435/222 |
| 3,728,224 | 4/1973 | Borglum | 435/222 |
| 3,740,318 | 6/1973 | Churchill et al. | 435/222 |
| 3,856,627 | 12/1974 | Nagasawa et al. | 435/253.6 |
| 4,086,136 | 4/1978 | Isowa et al. | 435/68.1 |
| 4,235,970 | 11/1980 | Leach et al. | 435/202 |
| 4,375,431 | 3/1983 | Bradford et al. | 435/68.1 |
| 4,863,857 | 9/1989 | Blalock et al. | 435/68.1 |
| 5,002,871 | 3/1991 | Iacobucci | 435/68.1 |
| 5,037,741 | 8/1991 | Iacobucci | 435/68.1 |

FOREIGN PATENT DOCUMENTS

| | | |
|---|---|---|
| 58-109425 | 6/1983 | Japan . |
| 58-177920 | 10/1983 | Japan . |
| 59-44323 | 3/1984 | Japan . |
| 59-44324 | 3/1984 | Japan . |
| 61-36226 | 2/1986 | Japan . |
| 61-36227 | 2/1986 | Japan . |

*Primary Examiner*—Herbert J. Lilling
*Attorney, Agent, or Firm*—Armstrong, Westerman, Hattori, McLeland & Naughton

[57] ABSTRACT

A method of producing an angiotensin converting enzyme inhibitor-containing composition, which is of value as an antihypertensive agent or diet, from natural resources. According to the method, proteins are hydrolyzed with a protease elaborated by a microorganism of the genus Bacillus, Aspergillus or Rhizopus or a protease of papaya origin.

5 Claims, No Drawings

METHOD FOR PRODUCING AN ANGIOTENSIN CONVERTING ENZYME INHIBITOR-CONTAINING COMPOSITION

FIELD OF THE INVENTION

The present invention relates to a method of producing an angiotensin converting enzyme inhibitor-containing composition from naturally-occurring materials, which composition is of value as, inter alia, an antihypertensive agent or an antihypertensive diet.

BACKGROUND OF THE INVENTION

Angiotensin converting enzyme (ACE) is an enzyme which is chiefly present in the lung, vascular endothelial cells and renal proximal tubules and acts on angiotensin I (Asp-Arg-Val-Tyr-Ile-His-Pro-Phe-His-Leu) to cleave a dipeptide ($His^9$-$Leu^{10}$) off its C-terminus to give rise to angiotensin II which has potent pressor activity.

Furthermore, this enzyme decomposes bradykinin, a physiological hypotensive substance, to inactivate it and, as such, is intimately involved in the pressor system. It has been considered that inhibition of ACE would lower the blood pressure and is, therefore, clinically useful for the prevention and treatment of hypertension.

Recently, since captopril, a proline derivative, was synthesized and found to have hypotensive activity, much research has been undertaken for synthesis of a variety of ACE inhibitors and it has also been attempted to isolate such substances from natural resources.

This is because natural type ACE inhibitors available from foods or food materials may be expected to be of value as antihypertensive agents of low toxicity and high safety.

However, it is rare that a potent ACE inhibitor is found in natural resources and all that are known at present are teprotide (a nonapeptide, SQ 20881) which was isolated from Brazilian and Japanese snake venoms and Metabolite IS83 of a Streptomyces organism. (Japanese Patent Laid-open No. 58-177920). As ACE inhibitors obtainable by enzymatic treatment of a natural material, the peptides obtainable by hydrolysis of milk casein with trypsin (Japanese Patent Laid-open No. 58-109425, No. 59-44323, No. 59-44324, No. 61-36226 and No. 61-36227) are known. Under the circumstances, development of new, more potent ACE inhibitors has been earnestly awaited.

SUMMARY OF THE INVENTION

In the course of screening for natural ACE inhibitors, the inventors of the present invention found peptides having ACE inhibitory activity in the hydrolyzates of proteins, particularly muscle proteins, fish meat, particularly dried bonito, pork, beef and poultry meat, which can be obtained with the proteases elaborated by microorganisms of the genus Bacillus, the genus Aspergillus or the genus Rhizopus, or a protease derived from papaya. The present invention has been developed on the basis of the above finding.

DETAILED DESCRIPTION OF THE INVENTION

The ACE inhibitor composition of the present invention can be obtained with particularly high efficiency when an enzyme of said microbial origin is employed, and a composition as potent as the composition of the invention cannot be obtained by the hydrolysis with the known enzymes.

The following is a list of microorganisms which elaborate the enzymes which can be employed in the present invention.

| | |
|---|---|
| Bacillus brevis | IFO 12333 |
| Bacillus cereus | IFO 13690 |
| Bacillus circulans | IFO 3329 |
| Bacillus coagulans | IFO 12583 |
| Bacillus licheniformis | IFO 12107 |
| Bacillus megaterium | IFO 13498 |
| Bacillus pumilus | IFO 3813 |
| Bacillus sphaericus | IFO 3341 |
| Bacillus stearothermophilus | IFO 13737 |
| Bacillus subtilis | IFO 3009 |
| Aspergillus niger | IFO 4407 |
| Rhizopus delemar | IFO 4746 |
| Aspergillus melleus | IFO 4420 |
| Aspergillus oryzae | IFO 4135 |

It should be understood that IFO is an acronym of Institute for Fermentation, Osaka and the above IFO numbers are accession numbers at the same institute. The culture strains deposited under these accession numbers are available from that institute upon request.

As the above-mentioned enzymes, the following commercial enzyme preparations can be employed with advantage in accordance with the invention.

The enzyme produced by *Bacillus subtilis*:

| | |
|---|---|
| Aloase AP-10 | (Yakult Honsha) |
| Orientase 90N | (Ueda Chemical Industries) |
| Protin PC10F | (Yamato Kasei) |
| Orientase 10B | (Ueda Chemical Industries) |
| Bioprase | (Nagase Sangyo) |
| Alcalase | (Novo Industry Japan) |
| Protease S | (Amano Pharmaceutical) |
| Proleser | (Amano Pharmaceutical) |

The enzyme produced by *Aspergillus niger*:

| | |
|---|---|
| Protease YP-SS | (Yakult Honsha) |
| Protin FA | (Yamato Kasei) |
| Morushin | (Seishin Pharmaceutical) |
| Denapsin | (Nagase Sangyo) |

The enzyme produced by *Aspergillus Oryzae*:

| | |
|---|---|
| Protease A | (Amano Pharmaceutical) |
| Denazyme AP | (Nagase Sangyo) |
| Pantidase NP-2 | (Yakult Honsha) |
| Sumizyme LP | (Shin Nihon Chemical Industries) |
| Protease M | (Amano Pharmaceutical) |

The enzyme produced by *Aspergillus melleus*:

| | |
|---|---|
| Protease P | (Amano Pharmaceutical) |
| Sumizyme MP | (Shin Nihon Chemical Industries) |

The enzyme produced by *Rhizopus delemar*:

| | |
|---|---|
| XP-415 | (Nagase Sangyo) |

The enzyme of papaya origin:

| | |
|---|---|
| Papain | (Nagase Sangyo) |
| Papain W40 | (Amano Pharmaceutical) |

The protein to be digested may be one of animal or microbial origin. Particularly useful proteins are muscle proteins, fish proteins such as bonito and bonito-derived proteins, sardine protein, and animal meats such as pork, beef, etc., and poultry meat.

The method for digesting such proteins with said enzyme in accordance with the invention is dependent on types of protein. In the case of a sparingly soluble protein, it is homogenized in hot water with vigorous stirring and the enzyme is added in a proportion of 0.005 to 10 weight percent, preferably 0.1 to 2 weight percent, based on the resulting protein solution. The mixture is then allowed to stand or stirred at a temperature of 5° to 90° C., preferably at 20° to 70° C., for 1 to 3 days until the protein has been hydrolyzed to a decomposition rate (peptide cleavage rate) of 5% or more. The pH of the system is maintained at pH 4 to 9, preferably 6 to 8, when a neutral protease is employed; at pH 0.1 to 4, preferably 0.5 to 3, when an acid protease is employed; or at pH 7 to 12, preferably 8 to 10, when an alkaline protease is employed.

The decomposition rate is expressed in the percentage of amino nitrogen relative to total nitrogen as determined by the method described in Journal of Agricultural and Food chemistry, 24, No. 6, 1090-1093 (1976).

The ACE inhibitor-containing composition thus obtained is a mixture of various peptides, mainly oligopeptides of the amino acid compositions Ile-Trp-His-His-Thr, Ala-Leu-Pro-His-Ala and Ile-Lys-Trp. These peptides may be used as such or further purified for use.

The route of administration of such peptides may for example be oral, parenteral or rectal but is preferably oral. The dosage of the peptide of the invention depends on the type of peptide, route of administration and the patient's condition and age, for instance, but is generally about 0.001 to 1000 mg, preferably 0.1 to 100 mg. This dose is administered 1 to 3 times a day.

The peptide according to the invention is generally administered as formulated with a pharmaceutically acceptable carrier. The carrier may be any of the ordinary carriers that are inert to the peptide, such as lactose, glucose, mannitol, dextrin, cyclodextrin, starch, sucrose, magnesium metasilicate aluminate, synthetic aluminum silicate, carboxymethylcellulose sodium, hydroxypropylstarch, carboxymethylcellulose calcium, ion exchange resins, methylcellulose, gelatin, gum arabic, hydroxypropylcellulose, hydroxypropylmethylcellulose, polyvinylpyrrolidone, polyvinyl alcohol, soft silicic anhydride, magnesium stearate, talc, gum tragacanth, bentonite, B gum, titanium dioxide, sorbitan fatty acid esters, sodium lauryl sulfate, glycerol, glycerol fatty acid esters, purified lanolin, glycerogelatin, polysorbate, macrogols, vegetable oils, waxes, liquid paraffin, white vaseline, fluorocarbons, nonionic surfactants, propylene glycol, water and so on. The dosage form may be a tablet, capsule, granule, powder, syrup, suspension or injectable solution. These preparations can be manufactured by the established pharmaceutical procedures. In the case of a liquid preparation, it may be a lyophilizate or the like which is extemporaneously reconstituted with a suitable vehicle such as water. The tablet and granule may be coated in the conventional manner. In the case of an injection, it can be prepared by dissolving the peptide of the invention in water. Where necessary, the peptide may be dissolved in physiological saline or a glucose solution. Such solutions may contain a buffer, a preservative and/or other additives.

These preparations may contain the peptide of the invention in a proportion of not less than 0.01% by weight and preferably 0.5 to 70% by weight. These preparations may further contain other therapeutically useful ingredients.

In accordance with the present invention, an ACE inhibitor composition of value as an antihypertensive agent or diet can be produced by hydrolyzing a protein with a certain enzyme produced by a microorganism or derived from a plant.

EXAMPLES

The following examples are further illustrative of the present invention.

Examples 1 through 19

To 5 g of dried bonito was added 45 ml of water and the mixture was thoroughly homogenized. Then, the protease shown in Table 1 was allowed to act upon the homogenate for hydrolysis reaction and the reaction mixture was centrifuged. The resulting supernatant was concentrated and the ACE inhibitory activity of the concentrate was determined.

Conditions of Enzymatic Digestion

When a neutral protease was used, the reaction system was adjusted with sodium hydroxide to pH 7.0, allowed to react at 37° C. for 13 hours and, then, boiled for 10 minutes. When an acid protease was employed, the reaction system was adjusted to pH 2.5 and the reaction was conducted at 37° C. for 3 hours, followed by 10 minutes' boiling. When an alkaline protease was used, the reaction system was adjusted with sodium hydroxide to pH 10.0, allowed to react at 37° C. for 3 hours and boiled for 10 minutes. The enzymes were invariably used in a proportion of 1/100 weight parts based on the dried bonito homogenate.

Assay of ACE Inhibitory Activity

The determination of ACE inhibitory activity was performed in accordance with the method of Cheung and Cushman [Biochemical Pharmacology, 20, 1637 (1971)] under the following conditions.

| | |
|---|---|
| Substrate: | Bz(benzyl)-Gly—His—Leu (86 mg dissolved in 8 ml water-8 ml phosphate buffer (500 mM, pH 8.3) containing 1.5 mM NaCl) |
| Enzyme: | Rabbit lung acetone powder (Sigma) (1 g pulverized in 10 ml of mM MM phosphate buffer pH 8.3 and centrifuged; the supernatant was used) |

One-hundred microliters of the above substrate was mixed with 12 μl of the enzyme solution and a predetermined amount of the peptide and the mixture was made up with water to make 250 μl. The reaction was conducted at 37° C. for 30 minutes.

The reaction was quenched with 250 μl of 1N-HCl. After completion of the reaction, 1.5 ml of ethyl acetate was added to the reaction mixture and the whole mixture was stirred in a vortex mixer for 15 seconds, after which it was centrifuged A 1.0 ml aliquot of the ethyl acetate layer was taken and the ethyl acetate was distilled off. The residue was dissolved in 1 ml of distilled water and the absorbance of extracted hippuric acid was determined at 228 nm ($OD_{228}$).

The inhibitory activity was expressed as the 50% inhibitory concentration [$IC_{50}$(μg/ml)] of the inhibitor (the peptide of the invention) with the $OD_{228}$ value in the absence of the inhibitor being taken as 100% ACE activity and the $OD_{228}$ value of the reaction system at reaction time 0 as 0%.

Examples 20 through 29

TABLE 1

| Example | Origin of protease | Commercial enzyme | $IC_{50}$ (μg/ml) |
|---|---|---|---|
| 1 | Bacillus subtilis | Aloase-10* | 98 |
| 2 | Bacillus subtilis | Aloase AP-10* | 96 |
| 3 | Bacillus subtilis | Protin PC10F* | 98 |
| 4 | Aspergillus niger | Protease YP-SS# | 83 |
| 5 | Aspergillus niger | Protin FA# | 99 |
| 6 | Aspergillus niger | Morushin# | 99 |
| 7 | Aspergillus niger | Denapsin# | 99 |
| 8 | Rhizopus delemar | XP-415# | 98 |
| 9 | Bacillus subtilis | Orientase 10B** | 71 |
| 10 | Bacillus subtilis | Alcalase** | 70 |
| 11 | Bacillus subtilis | Protease S** | 95 |
| 12 | Aspergillus melleus | Protease P* | 105 |
| 13 | Aspergillus melleus | Sumizyme MP* | 96 |
| 14 | Aspergillus oryzae | Protease A* | 110 |
| 15 | Aspergillus oryzae | Denazyme AP* | 99 |

TABLE 1-continued

| Example | Origin of protease | Commercial enzyme | $IC_{50}$ (μg/ml) |
|---|---|---|---|
| 16 | Aspergillus oryzae | Pantidase NP-2* | 98 |
| 17 | Aspergillus oryzae | Sumizyme LP* | 99 |
| 18 | Papaya | Papain* | 75 |
| 19 | Papaya | Papain W40* | 98 |

Note:
*Neutral protease
Acid protease
**Alkaline protease

As in Examples 1 through 19, proteins were digested with the enzymes produced by organisms of the genus Bacillus (all of which were neutral enzymes).

TABLE 2

| Example | Protein | Origin of protease | $IC_{50}$ (μg/ml) |
|---|---|---|---|
| 20 | Dried bonito | Bacillus brevis | 100 |
| 21 | Dried bonito | Bacillus cereus | 105 |
| 22 | Dried bonito | Bacillus circulans | 110 |
| 23 | Corb shell meat | Bacillus coagulans | 132 |
| 24 | Egg white | Bacillus licheniformis | 130 |
| 25 | Pork | Bacillus megaterium | 121 |
| 26 | Beef | Bacillus pumilus | 125 |
| 27 | Poultry meat | Bacillus sphaericus | 110 |
| 28 | Dried bonito | Bacillus stearothermophilus | 102 |
| 29 | Dried bonito | Bacillus subtilis | 95 |

What is claimed is:

1. A method of producing an angiotensin converting enzyme inhibitor peptide composition comprising Ile-Trp-His-His-Thr, Ala-Leu-Pro-His-Ala and Ile-Lys-Trp, said composition having an $IC_{50}$ value of 110 μg/ml or less, which comprises forming a solution by hydrolyzing dried bonito protein with water in the presence of a protease derived from a microorganism of the genus Bacillus, Aspergillus or Rhizopus, or a protease of papaya origin, and recovering the solution containing the peptide composition.

2. The method of claim 1 wherein the protease is derived from *Bacillus subtillis*.

3. The method of claim 1 wherein the enzyme is derived from *Aspergillus niger, Asperigllus oryzae* or *Aspergillus melleus*.

4. The method of claim 1 wherein the enzyme is derived from *Rhizopus delemar*.

5. The method of claim 1 wherein the solution containing the peptide composition is formulated with a pharmaceutically acceptable carrier.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
( A ) ORGANISM: Homo sapiens ( x i ) SEQUENCE DESCRIPTION: SEQ ID NO:1:

Asp Arg Val Tyr Ile His Pro Phe His Leu
1               5                   10

( 2 ) INFORMATION FOR SEQ ID NO:2:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
( A ) ORGANISM: Homo sapiens ( x i ) SEQUENCE DESCRIPTION: SEQ ID NO:2:

```
Asp Arg Val Tyr Ile His Pro Phe
1               5
```

(2) INFORMATION FOR SEQ ID NO:3:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:3:

```
Ile Trp His His Thr
1               5
```

(2) INFORMATION FOR SEQ ID NO:4:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:4:

```
Ala Leu Pro His Ala
1               5
```

(2) INFORMATION FOR SEQ ID NO:5:

(i) SEQUENCE CHARACTERISTICS:
        (A) LENGTH: 3 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:5:

```
Ile Lys Trp
1
```